(12) United States Patent
Ohta et al.

(10) Patent No.: US 7,507,805 B2
(45) Date of Patent: Mar. 24, 2009

(54) CELL DEATH-INDUCING FUSED GENE ACTING SPECIFICALLY ON CANCER AND GENE PRODUCT THEREOF

(75) Inventors: Shigeo Ohta, Tokyo (JP); Sadamitsu Asoh, Tokyo (JP)

(73) Assignee: Nippon Medical School Foundation, Tokyo (JP)

( * ) Notice: Subject to any disclaimer, the term of this patent is extended or adjusted under 35 U.S.C. 154(b) by 389 days.

(21) Appl. No.: 10/550,280

(22) PCT Filed: Mar. 23, 2004

(86) PCT No.: PCT/JP2004/003956

§ 371 (c)(1),
(2), (4) Date: Sep. 23, 2005

(87) PCT Pub. No.: WO2004/085653

PCT Pub. Date: Oct. 7, 2004

(65) Prior Publication Data

US 2006/0234928 A1    Oct. 19, 2006

(30) Foreign Application Priority Data

Mar. 24, 2003    (JP) ............................. 2003-081337

(51) Int. Cl.
*C07H 21/04* (2006.01)

(52) U.S. Cl. ..................................................... 536/23.5
(58) Field of Classification Search ........................ None
See application file for complete search history.

(56) References Cited

FOREIGN PATENT DOCUMENTS

| JP | 2002-355034 | 12/2002 |
|---|---|---|
| WO | 00/42973 | 7/2000 |
| WO | 01/53342 | 7/2001 |

OTHER PUBLICATIONS

Ishibashi et al (Biochem Biophys Res Commun. Feb. 13, 1998; 243 (2):609-616).*
P. L. Simonian et al., "Bax Homodimerization is not Required for Bax to Accelerate Chemotherapy-Induced Cell Death", The Journal of Biological Chemistry, vol. 271, No. 50, pp. 32073-32077, Dec. 13, 1996.
N. P. Mahajan et al., "Bcl-2 and Bax Interactions in Mitochondria Probed with Green Fluorescent Protein and Fluorescence Resonance Energy Transfer", Nature Biotechnology, vol. 16, pp. 547-552, Jun. 1998.
K. Usui et al., "N-Terminal Deletion Augments the Cell-Death-Inducing Activity of Bax in Adenoviral Gene Delivery to Nonsmall Cell Lung Cancers", Oncogene, vol. 22, p. 2655-2663, 2003.
J. Gu et al., "A novel single tetracycline-regulative adenoviral receptor for tumor-specific *Bax* gene expression and cell killing in vitro and in vivo", Oncogene, vol. 21, No. 31, pp. 4757-4764, 2002.
X. Li et al., "Overexpression of BCL-$X_L$ Underlies the Molecular Basis for Resistance to Staurosporine-induced Apoptosis PC-3 Cells", Cancer Research, vol. 61, No. 4, pp. 1699-1706, 2001.
H. Ellerby et al., "Anti-cancer activity of targeted pro-apoptotic peptides", Nature Medicine, vol. 5, No. 9, pp. 1032-1038, Sep. 1999.
T. Aokage et al., "Green fluorescent protein causes mitochondria to aggregate in the presence of the Bcl-2 family proteins", Biochemical and Biophysical Research Communications, vol. 314, No. 3, pp. 711-716, Feb. 2004.

* cited by examiner

*Primary Examiner*—Christopher H Yaen
(74) *Attorney, Agent, or Firm*—Wenderoth, Lind & Ponack, L.L.P.

(57) ABSTRACT

The present invention provides a protein having a potent cell-death inducing activity that is, a fused protein is in which a modified Bax protein fused with GFP at the N-terminus and is further fused with a homing signal peptide having a homing activity specific for endothelial cells in tumor angiogenesis; a gene coding the fused protein; and a cancer cell growth inhibitor containing the fused protein. Namely, a fused gene containing a cell death-inducing gene acting specially on cancer tissue, which is a fused gene having a gene encoding a homing signal peptide sequence specific for endothelial cells undergoing angiogenesis, a gene encoding a green fluorescent protein (GFP) and a gene encoding ΔNBax protein, which is human Bax with a deletion of the N-terminal sequence containing the BH3 domain in this order, and a fusion protein encoded by the fused gene.

6 Claims, 4 Drawing Sheets

CELL DEATH-INDUCING FUSED GENE ACTING SPECIFICALLY ON CANCER AND GENE PRODUCT THEREOF

This application is a 371 U.S. national stage of International Application No. PCT/JP2004/003956 filed Mar. 23, 2004, incorporated by reference in its entirety.

TECHNICAL FIELD

The present invention relates to a protein having a strong cell death-inducing activity, that is, a fusion protein in which a modified Bax protein is fused with GFP at the N-terminus to construct a GFP-modified Bax protein and a homing signal peptide having a homing activity to a surface receptor of endothelial cells undergoing angiogenesis is further fused with the GFP-modified Bax protein at the N-terminus. The present invention also relates to a gene which codes for the protein and a drug which contains the protein to inhibit the growth of cancer cells.

BACKGROUND ART

Apoptosis is programmed cell death and the Bax gene is known to be a potent apoptosis-inducing gene. The Bcl-2 gene is known to be an oncogene which suppresses apoptosis and many Bcl-2 family proteins homologous to Bcl-2 protein are found (Bcl-2, Bcl-$x_L$ and the like).

Introducing genes that induce various types of cell death including apoptosis into cancer cells is a promising anticancer therapy. It has been reported recently that Bcl-2 family proteins such as Bcl-2, Bcl-$x_L$ and the like are expressed in cancer cells and exhibit antagonism to the induction of cell death by the Bax protein. These family proteins exhibit antagonism by binding to Bax protein via the region named BH3 of the Bax protein. The present inventors investigated an N-terminus deleted Bax (ΔNBax) which comprises an amino acid sequence from the 112th amino acid residue to the 192nd amino acid residue of Bax and has lost the N-terminal region including the BH3 region, and reported that ΔNBax is the cell death-inducing domain of the cell death-inducing bax gene product (Biochem Biophys Res Commun. 1998 Feb. 13; 243 (2): 609-616). When located at the downstream of a promoter, expression of the ΔNBax in cells induces cell death, which can not be inhibited by even overexpression of Bcl-$x_L$. The gene coding for ΔNBax, the vector containing the gene and the usage of the ΔNBax peptide for inhibiting the proliferation of cancer cells have been reported (JP Patent Publication (Kokai) No. 2002-355034).

On another front, various homing signal peptides are currently investigated to introduce drugs, such as anti-cancer drugs and the like, into cells specifically. For example, peptides designated as NGR and RGD are known to act selectively on the endothelial cells undergoing angiogenesis (Nat Med. 1999 September; 5(9):1032-1038), and it is possible to use these as specific homing signal peptides for the cell surface receptor of endothelial cells undergoing angiogenesis in cancer tissue.

Presently, cancer is treated mainly by chemotherapy in which anti-cancer drugs are administered, radiotherapy in which an affected lesion is irradiated, immunotherapy in which anti-cancer cell antibodies are administered and gene therapy. However, there are various problematic side effects in chemotherapy and radiation therapy. Also, immunotherapy requires a long period of time and further, gene therapy demands great efforts in developing because of the safety considerations such as uncertainty of the effect of the gene on patients and the like. Thus, cancer therapy in which a large-molecular-weight protein acting directly on cancer cells is directly targeted to the target site has been sought. However, there has been no protein which specifically acts on cancer cells to strongly inhibit the growth of cancer cells and can be surely used for treating cancer. If ΔNBax is specifically interacted with the surface receptor of the endothelial cells undergoing angiogenesis in cancer tissue, it is expected that ΔNBax is utilized as a more effective inhibitor of cancer cell growth, solving the shortcomings of the past treatment method. However, no investigation in this line has conventionally been carried out. ΔNBax itself possesses an apoptosis-inducing activity but its apoptosis-inducing activity has been desired to be enhanced.

DISCLOSURE OF THE INVENTION

The objective of the present invention is to enhance the apoptosis-inducing activity of ΔNBax, which is a modified Bax, and further to let ΔNBax act specifically on the cell surface receptor of the endothelial cells undergoing angiogenesis. In particular, the objective of the present invention is to provide a fused protein, in which a homing signal peptide that is specific to the cell surface receptor of endothelial cells undergoing angiogenesis, Green Fluorescent Protein (GFP) and ΔNBax are fused in this order, and a gene coding for the fused protein and an anti-cancer drug consisting of the same.

The present inventors, to investigate the effect of ΔNBax, have constructed a fusion protein, in which GFP is fused to the N-terminus of ΔNBax to easily visualize the localization of ΔNBax in the cells, and introduced the fusion protein to established cell lines to investigate cell death-inducing activity. Surprisingly, it was discovered that the cell death-inducing activity was enhanced in ΔNBax fused with GFP. Furthermore, the present inventors, having investigated earnestly how GFP-fused ΔNBax with enhanced apoptosis-inducing activity is directed to specifically interact with the surface receptor of the endothelial cells undergoing angiogenesis in cancer tissue, have discovered that GFP-fused ΔNBax with enhanced apoptosis-inducing activity can specifically interacts with the surface receptor of the endothelial cells undergoing angiogenesis by fusing the homing signal peptide such as NGR, RGD and the like to the N-terminus of GFP-fused ΔNBax, completing the present invention.

Thus the present invention is as follows.
(1) A fusion gene comprising a cell death-inducing gene that acts specifically on a surface receptor of endothelial cells undergoing angiogenesis, wherein the fusion gene is produced by fusing, a gene that codes for a homing signal peptide sequence specific for the surface receptor of endothelial cells undergoing angiogenesis, a gene coding for green fluorescent protein (GFP) and a gene coding for ΔNBax protein, which is human Bax with a deletion of the N-terminal sequence including the BH3 region, in this order.
(2) The fusion gene according to (1), wherein the homing signal peptide sequence is selected from the group consisting of peptide sequences of (a) to (o) shown below:
(a) RGD peptide sequence,
(b) NGR peptide sequence,
(c) peptide sequence shown in SEQ ID NO: 7,
(d) peptide sequence shown in SEQ ID NO: 8,
(e) peptide sequence shown in SEQ ID NO: 9,
(f) peptide sequence shown in SEQ ID NO: 10,
(g) peptide sequence shown in SEQ ID NO: 11,
(h) peptide sequence shown in SEQ ID NO: 12,
(i) peptide sequence shown in SEQ ID NO: 13, (j) peptide sequence shown in SEQ ID NO: 14,
(k) peptide sequence shown in SEQ ID NO: 15,
(l) peptide sequence shown in SEQ ID NO: 16,
(m) peptide sequence comprising LDV,
(n) peptide sequence shown in SEQ ID NO: 17 and
(o) peptide sequence shown in SEQ ID NO: 18.
(3) The fusion gene according to (2), wherein the homing signal peptide sequence is RGD or NGR which is a homing signal peptide specific for endothelial cells undergoing angiogenesis.
(4) The fusion gene according to any of (1)-(3), wherein ΔNBax protein, which is human Bax with a deletion of the N-terminal sequence containing the BH3 domain, comprises an amino acid sequence from the 112th to 192nd of the human BAX amino acid sequence.
(5) The fusion gene according to any of (1)-(3), wherein the fusion gene comprises following DNA of (p) or (q),
(p) a DNA having a nucleotide sequence of SEQ ID NO: 3 or SEQ ID NO: 5.
(q) a DNA which hybridizes with a DNA having a complementary sequence of the DNA of (p) under a stringent condition and which codes for a protein which binds to endothelial cells undergoing angiogenesis and which has an enhanced cell death-inducing activity.
(6) An expression vector containing the fusion gene according to any of (1) to (5).
(7) The expression vector according to (6), which can express the fusion gene in a cell-free system.
(8) A method for producing the fusion protein encoded by any of the fusion gene according to (1) to (5), including a step of in vitro expression by the expression vector according to (7).
(9) A fusion protein containing a cell death-inducing protein that acts specifically on surface receptor of endothelial cells undergoing angiogenesis, wherein the fusion protein is generated by fusing, a homing signal peptide sequence specific for a surface receptor of endothelial cells undergoing angiogenesis, green fluorescent protein (GFP) and ΔNBax protein, which is human Bax with a deletion of the N-terminal sequence containing the BH3 domain, in this order.
(10). The fusion protein according to (9), wherein the homing signal peptide sequence is selected from the group consisting of peptide sequences of (a) to (o) shown below:
(a) RGD peptide sequence,
(b) NGR peptide sequence,
(c) peptide sequence shown in SEQ ID NO: 7,
(d) peptide sequence shown in SEQ ID NO: 8,
(e) peptide sequence shown in SEQ ID NO: 9,
(f) peptide sequence shown in SEQ ID NO: 10,
(g) peptide sequence shown in SEQ ID NO: 11,
(h) peptide sequence shown in SEQ ID NO: 12,
(i) peptide sequence shown in SEQ ID NO: 13,
(j) peptide sequence shown in SEQ ID NO: 14,
(k) peptide sequence shown in SEQ ID NO: 15,
(l) peptide sequence shown in SEQ ID NO: 16,
(m) peptide sequence comprising LDV,
(n) peptide sequence shown in SEQ ID NO: 17 and
(o) peptide sequence shown in SEQ ID NO: 18.
(11) The fusion protein according to (10), wherein the homing signal peptide sequence is RGD or NGR which is a homing signal peptide sequence specific for endothelial cells undergoing angiogenesis.
(12) The fusion protein according to (10) or (11), wherein ΔNBax protein, which is human Bax with a deletion of the N-terminal sequence containing the BH3 domain, consists of an amino acid sequence from the 112th to 192nd of the human BAX amino acid sequence.
(13) The fusion protein according to any of (10) to (12) shown in (r) or (s) below,
(r) a fusion protein having an amino acid sequence which is represented by SEQ ID NO: 4 or 6,
(s) a protein, which has the amino acid sequence of (r) in which one or some amino acids are deleted, substituted or added, and which binds to endothelial cells undergoing angiogenesis and has enhanced cell death-inducing activity.
(14) A cancer cell growth inhibitor containing the fusion protein according to any one of (10) to (13), and
(15) The cancer cell growth inhibitor according to (14), wherein the cell death-inducing activity of ΔNBax protein, which is human Bax with a deletion of the N-terminal sequence containing the BH3 domain, is enhanced by fusion with green fluorescent protein (GFP) as compared with that of ΔNBax protein, which is human Bax with only the N-terminal sequence containing the BH3 domain deleted.

This application incorporates herein the content of the description of JP Patent Application No. 2003-081337 and/or drawings on which the priority of the present application is based.

BEST MODE FOR CARRYING OUT THE INVENTION

Figure 1:
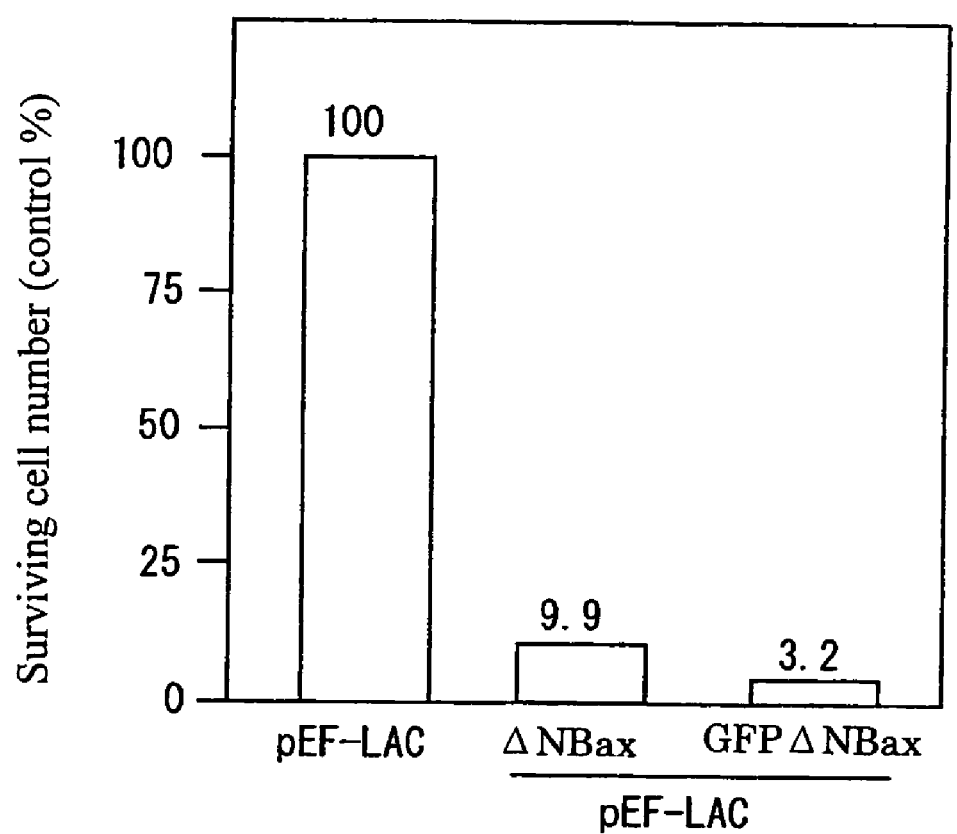
FIG. 1 shows the result of the comparison of cell death-inducing activity of GFP-ΔNBax and ΔNBax.

The invention of this application is a fusion gene containing the cell death-inducing region of the cell death-inducing gene, human Bax, and a protein encoded by this gene, wherein the fusion gene contains a gene which codes for a homing signal peptide and a gene which codes for GFP (green fluorescent protein) and is constructed by ligating the gene coding for the homing signal peptide, the GFP coding gene and the cell death-inducing region of Bax from the 5' end in this order.

Bax contains BH1, BH2 and BH3 domains, but the region responsible for the cell death-inducing activity of Bax is the area outside the BH3 domain. The Blc-2 family proteins, which antagonize the cell death-inducing activity of Bax protein, interacts with the BH3 domain. The core sequence of the BH3 domain is from the 59th to 73rd or 77th residue of the N-terminal amino acid sequence of Bax. The modified Bax (ΔNBax) is encoded by the gene which contains the cell death-inducing region and has the nucleotide sequence corresponding at least the N-terminal amino acid sequence from the 59th to 73rd or 77th amino acids deleted. As the gene coding for such a modified Bax containing the cell death-inducing region, this is preferably a polynucleotide of 243 bases which encodes the sequence of amino acid residues from residue 112 to residue 192 of the amino acid sequence of the Bax protein which consist of 192 amino acid residues and which is encoded by the Bax gene. The nucleotide sequence of the human Bax gene and the amino acid sequence of human Bax protein are shown in SEQ ID NO: 1 and SEQ ID NO: 2, respectively. Based on these sequence information, human Bax cDNA is synthesized by conventional genetic engineering technique and ΔNBax can be obtained using restriction enzymes and the like. For example, the method described in Biochem Biophys Res Commun. 1998 Feb. 13: 243 (2): 609-616 can be used to obtain ΔNBax.

In the present invention, the ΔNBax gene is preferably a DNA which consists of a nucleotide sequence from nucleotide 334 to nucleotide 576 of SEQ ID NO: 1 (corresponding to residue 112 to residue 192 of the amino acid sequence of Bax protein) but also includes genes which hybridize with a DNA complementary to this DNA under a stringent condition and which also code for a protein having the cell death-inducing activity. The stringent conditions are, for example, that the sodium concentration is 500 to 1000 mM, preferably 700 mM, the temperature is 50 to 70° C., preferably 65° C. The ΔNBax gene includes DNA, which has homology to the nucleotide sequence from nucleotide 334 to nucleotide 576 of SEQ ID NO: 1 of at least 85% or above, preferably 90% or above, more preferably 95% or above and especially preferably 97% or above, when calculated by BLAST (Basic Local Alignment Search Tool) or the like (for example, using the parameters of the initial or default setting) and also codes for a protein with the cell death-inducing activity. Further, the gene includes DNA in which one or more nucleotides in the nucleotide sequence from nucleotide 334 to nucleotide 576 of SEQ ID NO: 1 are deleted, substituted or added and which also codes for a protein having the cell death-inducing activity. The term "cell death-inducing activity" used herein means the activity of inducing cell death to cells, where cell death includes apoptosis and necrosis. For example, in one form of cell death, apoptosis, the characteristic morphological alterations occur such as chromosomal condensation in the cell nucleus, fragmentation of cell nucleus, loss of cell surface microvilli and condensation of cytoplasm. Originally, Bax has been found as a protein that induces apoptosis, but it has been reported that Bax causes necrosis in certain cell types (Shinomura, N., et al. Oncogene, Vol. 18:5703 (1999)). The term "cell death" used herein includes both of apoptosis and necrosis. It can be determined in vitro by the method according to Example 4 of the present description whether a particular protein has cell death-inducing activity or not.

GFP derived from the jellyfish *Aequorea victoria*, which is encoded by the gfp10gene of the jellyfish *Aequorea Victoria*, can be used (Prasher, D. C. et al. (1992), "Primary structure of the *Aequorea victoria* green fluorescent protein" Gene 111: 229-233). Also, the commercially available GFP gene can be used. For example the gene coding for GFP included in a commercially available vector pGreenlantern (Invitrogene LifeTechnology) (JP Patent Publication (Kohyo) No. 2000-503536) can be used. The GFP-coding sequence is shown in SEQ ID NO: 3 from nucleotide 40 to nucleotide 753 (from nucleotide 28 to nucleotide 741 in SEQ ID NO: 5). Various modified types of GFP are also known and these modified types of GFP may be used as the GFP in the present invention. These modified types of GFP include EGFP (enhanced green fluorescent protein), GFPUV, GFPmut3.1, BFP2 (all are available from Clonetech Co.), Venus (Nature Biotechnology January 20002 Vol. 20-1, 87-90) and S65T. Mutant forms of the GFP protein that emit lights of different color, such as EBFP (blue), ECFP (Cyan) and EYFP (Yellow) (all available from Clonetech Co.) may also be used as GFP in the present invention. These modified types of GFP are described in detail in, for example, "Experimental Course 3 in Post Genome Era, GFP and Bio-imaging, Supplement of Experimental Medicine" (Ed. by Miyawaki, Atsushi. Issued on Oct. 25, 2000, from Yodosha Co., Tokyo) and can be obtained by referring to this article. Further, a GFP modified to enhance the cell death-inducing activity of ΔNBax when fused with ΔNBax, and its derivative protein are also included as GFP in the present invention.

A homing signal peptide is a peptide which binds to its cognate receptor(s) (ligand for the homing signal peptide) expressed on the surface of particular cells, and when it is administered into the body, it is circulated in the body fluid and binds to the target cells carrying the receptor on their surface. The homing signal peptide can bind specifically to the receptor of the target cells. When a potential drug protein or the like are bound to the C-terminus of the homing signal peptide, the homing signal peptide carries this protein to the target cells, and this protein is incorporated into the cells. In the invention of the present application, a peptide is used which specifically binds to endothelial cells undergoing angiogenesis by binding specifically to the surface receptor of endothelial cells undergoing angiogenesis. NGR and RGD, which specifically bind to the homing signal peptide receptor of endothelial cells undergoing angiogenesis (Nat Med. 1999 September; 5 (9): 1032-1038), can be used as the homing signal peptide and the nucleotide sequences of NGR and RGD are shown by the nucleotide sequences in SEQ ID NO: 3, from nucleotide 4 to nucleotide 33 and SEQ ID NO: 5, from nucleotide 7 to nucleotide 21, respectively. It is known that NGR binds to Aminopeptidase N (CD13) (Pasqualini, R., et al., Cancer Research (2000) 60: 722-727, and RGD binds to αvβ3 and αvβ5 of integrin (Koivunen, E., et al., Bio/Technology (1995) 13: 265-270). Since NGR or RGD, when used as the homing signal peptide, homes directly to endothelial cells undergoing angiogenesis, cell death-inducing protein fused with the homing signal peptide binds to the surface receptor of endothelial cells undergoing angiogenesis in cancer tissues, is incorporated into those endothelial cells and causes the death of cells undergoing angiogenesis in cancer tissue. Since cancer cells in cancer tissue are provided with nutrients needed for survival and growth from endothelial cells undergoing angiogenesis, the cancer cells die because they can not be provided with nutrients due to the death of these endotherial cells. Thus, cell death-inducing protein fused with the homing signal peptide has killing effect on cancer cells at the final stage. Some cancer cells, after dedifferentiation, may express the receptor which is expressed on the surface of endothelial cells undergoing angiogenesis. In such cases, the homing signal peptide directly binds to the cancer cells, and the cell death-inducing protein is incorporated into the cancer cells causing the death of the cancer cells. It has been reported, for example, that NGR described above binds to KS1767 cancer cells derived from Kaposi sarcoma (Ellerby, H. M., et al. Nature medicine Vol. 5: 1032 (1999)), and therefore, the fusion protein with fused NGR of the present invention can cause directly the death of the cancer cells. However, the homing signal peptide is not limited to these peptides, but various peptides, which specifically bind to cells in particular tissues or organs, may be used for homing to cancer tissue of these tissue or organs. Examples of such peptides include followings.

(1) Organ specific homing signal peptides (Pasqualini, R. & Rouslahti, E. (Nature 1996 vol. 380, pp. 364-366.))

(a) The 4 signals, CLSSRLDAC (SEQ ID NO: 7), CNSRLHLRC (SEQ ID NO: 8), CENWWGDVC (SEQ ID NO: 9), WRCVLREGPAGGCAWFNRHRL (SEQ ID NO: 10) target the brain.

(b) The 2 signals CLPVASC (SEQ ID NO: 11), and CGAREMC (SEQ ID NO: 12) target the kidney.

(2) A homing signal peptide which targets synovial membrane (of the joints) (Lee, L. et al., Arthritis Rheum (2002) vol. 476, pp. 2109-2120.).
CKSTHDRLC (SEQ ID NO: 13)
(3) A homing signal peptide which targets tumor lymphatics (Laakkonen, P., et al., Nature Medicine (2002) vol. 8, pp. 751-755.).
CGNKRTRGC (SEQ ID NO: 14)
(4) A homing signal peptide which targets endothelial cells in blood vessels undergoing angiogenesis (Asai, T., et al., FEBS Letter (2002) vol. 520, pp. 167-170.).
APRPG (SEQ ID NO: 15)
(5) Peptides which bind to cell surface integrin (integrin is a collective name, and there are many different types of integrin) (Koivunen, E., et al., Method in Enzymology (1994) vol. 245, pp. 346-369.).
4 peptides, KQAGDV (SEQ ID NO: 16), LDV, KRLDGS (SEQ ID NO: 17), DGEA (SEQ ID NO: 18) are known.

Anti-cancer antigen antibodies which bind to cancer antigen or fragments of these antibodies may also be used in the present invention as a homing peptide because these antibodies and their fragments have a homing activity similar to that of the homing signal peptide.

The part of Bax containing its cell death-inducing region, GFP and the homing signal peptide are fused in the order so that the homing signal peptide is located at the N-terminus of the resultant protein, GFP is located next to the C-terminus of the homing signal peptide and the part of Bax containing its cell death-inducing region is located next to the C-terminus of GFP. This is designed because the homing signal peptide can bring protein that attached to the C-terminus of the homing signal peptide into the target cells and Bax contains also a membrane anchor region at the C-terminus. ΔNBax alone has the cell death-inducing activity and this activity is enhanced by fusing GFP to the N-terminus of ΔNBax. In the present invention, the enhanced cell death-inducing activity of the GFP-ΔNBax fusion protein means that its cell death-inducing activity is higher than that of ΔNBax alone. The higher activity of the cell death-inducing activity of the GFP-ΔNBax fusion protein can be determined by comparing the cell death-inducing activity of the GFP-ΔNBax with that of ΔNBax alone according to the method described in Example 1 (2) of the present description. For example, an appropriate expression vector containing the GFP-ΔNBax fusion gene or the ΔNBax alone is introduced into suitable host cells to express the GFP-ΔNBax fusion protein or ΔNBax protein alone. When the cell death-inducing activity is measured by the ratio of surviving cells, the cell death-inducing activity of the GFP-ΔNBax fusion protein is significantly stronger than that of ΔNBax alone, preferably 1.5 times stronger or above (the surviving cell ratio in the ΔNBax expression experiment is 1.5 times higher or above than that in the GFP-ΔNBax expression experiment), more preferably 2 times stronger or above, and especially 3 times stronger or above.

The fusion of the genes coding for the homing signal peptide, GFP and the cell death-inducing region of ΔNBax can be carried out by conventional genetic engineering techniques. At this time, appropriate restriction enzyme sites may be introduced and used to construct the fusion gene. As described above, the fusion is carried out in the order of: the gene coding for the homing signal peptide; the gene coding for GFP; and the gene coding for the cell death-inducing region of Bax. Here, care should be taken so that no stop codon emerges in the fused genes. The distance between the fused gene is not limited, and a linker sequence may be placed between them. The 3 genes should be fused in-frame in order that the fusion protein is translated to exhibit the horning activity and the enhanced cell death-inducing activity. SEQ ID NO: 3 shows the nucleotide sequence of the gene coding for the fusion protein which contains RGD as the homing signal peptide and ΔNBax consisting of an amino acid sequence from residue 112 to residue 192 of human Bax protein. SEQ ID NO: 5 shows the nucleotide sequence of the gene coding for the fusion protein which contains NGR as the homing signal peptide and ΔNBax consisting of the amino acid sequence from residue 112 to residue 192 of human Bax protein. Genes containing a DNA sequence which hybridize with the sequence complementary to the DNA sequence described above under stringent conditions, and whose products bind to endothelial cells undergoing angiogenesis and demonstrate stronger cell death-inducing activity than ΔNBax alone, are included in the present invention. The stringent conditions are, for example, that the sodium concentration is 500-1000 mM, preferably 700 mM, the temperature is 50-70° C., preferably 65° C. Also included in the present invention are genes containing DNA, which has homology to of the nucleotide sequence shown in SEQ ID NO: 3 or 5 of at least 85% or above, preferably 90% or above, more preferably 95% or above and especially preferably 97% or above when calculated by BLAST or the like (for example, using the parameters of the initial setting which is the default setting), which codes for a fusion protein which binds to endothelial cell undergoing angiogenesis and which has stronger cell death-inducing activity than ΔNBax alone. Further, included in the present invention is genes containing DNA in which one or more of the nucleotides in the nucleotide sequence of SEQ ID NO: 1 are deleted, substituted or added and which also codes for a protein which binds to endothelial cells undergoing angiogenesis and which has stronger cell death-inducing activity than ΔNBax alone.

In cases where homing signal peptides other than RGD and NGR are used, the fusion gene of the present invention includes a fusion gene which has a sequence with deletion, substitution or addition of some nucleotides as mentioned above, as long as a resultant fusion protein binds to target cells to exhibit the enhanced cell death-inducing activity.

The fusion gene constructed as described above can be cloned into an available appropriate expression vector to express, recover and purify the fusion. Here, it is preferable to express the fusion protein in a cell-free expression system because, when the expression vector is introduced into host cells to express the fusion protein, the host cells easily die due to the action of cell death-inducing activity of ΔNBax. The cell-free expression system herein means to express the gene product in the expression vector containing the gene in vitro by mixing the vector with required reagents in a appropriate container, without introducing the vector to host cells (Spirin, A. S. et al., (1988) "A continuous cell-free translation system capable of production polypeptides in high yield" Science 242, 1162; Kim, D. M., et al., (1996) "A highly efficient cell-free protein synthesis system from *E. coli*" Eur. J. Biochem. 239, 881-886). Protein can be expressed using a commercially available cell-free expression kit. Such kits include, for example, Rapid Translation System (RTS) (Roche) and Expressway In Vitro Protein Synthesis System (Invitrogen) and the like. In using these kits, the expression vector to be used is not limited, but there are suitable vectors for each cell free expression kit and these may be used. The expression vector for the former kit includes pIVEX2.2bNde, and the expression vector for the latter kit includes pEXP1 and pEXP2.

In in vivo expression system, where the expression vector containing the fusion gene of the present invention is introduced into host cells to express the fusion protein of the present invention, the host cells can not grow due to cell death by the effect of cell death-inducing protein when the fusion gene is constitutively expressed. Therefore, it is necessary to use host cells suitable for an inducible gene expression system so that induction of the fusion gene expression is controlled to allow the expression during the period from just after the host cells sufficiently grow until cell death is caused by the expressed fusion protein. By using the host cells suitable for the inducible expression system, induction of the expression, when the host cells containing the fusion gene grow to reach a sufficient number of cells, allows to obtain a sufficient amount of fusion protein until cell death of the host cells occurs. A vector capable of inducible expression of the gene is the vector in which the expression of the inserted exogenous gene is induced by a particular treatment. For example, an inducible expression vector can be constructed by introducing a promoter that is inducible or repressible by a particular regulatory agent or temperature condition into a vector. Some promoters are known to be inducible in a inducer-specific manner, when an inducer is added to the culture medium of host cells. For example, the lac promoter and the tac promoter is inducible by isopropyl-β-D-thiogalactopyranoside (IPTG). IPTG is also used as an inducer for T7 RNA polymerase in the T7 promoter system when T7 RNA polymerase DNA (T7 DNA1) is linked to the downstream of the lac promoter. Further, expression of the trp promoter is inducible by 3β-indolyl acrylic acid. Gene expression can be induced not only by addition of an inducer but also by changing the temperature of the culture. The recombinant host cells which express λcIts repressor and carry an expression vector containing $\lambda P_L$-promoter is cultured, for example, at about 15-36° C., preferably about 30-36° C. and then the induction of gene expression is preferably carried out by inactivating λcIts repressor at about 37-42° C. When T7 RNA polymerase DNA (T7 DNA1) in the T7 promoter system is linked to the downstream of the $\lambda P_L$-promoter, the T7 promoter is activated by binding of T7 phage RNA polymerase 1 generated by raising the culture temperature.

Further, cells resistant to the cell death-inducing protein may be used as host cells. For example, *Escherichia coli* (*E. coli*) cells and the like that are resistant to ΔNBax may be used. Such resistant bacteria can be obtained by inducing mutation by chemical mutagens such as N-methyl-N'-nitro-N-nitrosoguanidine and the like or physical mutagens such as ultraviolet light and the like and screening for the bacteria resistant to the cell-death-inducing protein. For example, when the recombinant *E. coli* cell carrrying the fusion gene of the present invention is artificially mutagenized, the bacterial cells that can grow are mutant *E. coli* cells resistant to ΔNBax. After introduction of a gene encoding ΔNBax (or the fusion gene of the present invention) into *E. coli* cells which are artificially mutagenized, the cells which can grow are mutant *E. coli* cells resistant to ΔNBax. Chemical and physical mutagens which cause mutation in genes, and the method of usage and dose of the mutagens are known to those skilled in the art, and the method for screening for the resistant cells may be designed appropriately by those skilled in the art.

Expression of the fusion protein by introducing the expression vector containing the fusion gene according to the present invention into host cells is carried out as follows.

Any vector derived from plasmid, phage, virus and the like, which are capable of replication in host cells, may be used. Vectors include, for example, *E. coli* plasmids, such as pBR322, pBR325, pUC118, pUC119, pKC30, pCFM536 and the like, *Bacillus subtilis* plasmids, such as pUB110 and the like, yeast plasmids, such as pG-1, YEp13, YCp50 and the like, phage vectors, such as λgt110, λZAPII and the like. Expression vectors for mammalian cells include virus DNA such as baculovirus, vaccinia virus, adeno virus and the like, SV40 and its derivatives. The vectors may contain an origin of replication, selection marker and promoter, and if necessary, an enhancer, a terminator, a ribosomal binding site, a poly-adenylation signal and the like. As described above, an inducible promoter should be used to induce the expression of the inserted gene.

The vectors which can be used include commercially available ones, for example, bacterial vectors such as pEF1, pPROEX (Invitrogen), pQE30, pQE31, pQE32, pQE70, pQE60, pQE-9 (Qiagen), pGEX-5X-1, pGEX-5X-2, pGEX-5X-3, pBluescriptII KS, ptrc99a, pKK223-3, pDR540, pRIT2T (Pharmacia), pET3a, pET3b, pET3c, pET-11a (Novagene), pUC118 (Takara), and eukaryotic vectors such as pXT1, pSG5 (Stratagene), pSVK3, pBPV, pMSG, pSVL, SV40 (Pharmcia) and the like.

The replication origins which can be used for the *E. coli* vectors include, for example, those of Col E1, R factor and F factor, those for the yeast vectors include, for example, those of 2 μm DNA and ARSI, and those for the mammalian vectors include, for example, those of SV40, adenovirus and bovine papilloma virus. The promoters which can be used include adenovirus or SV40 promoter, *E. coli* lac or trp promoter, phage lambda $P_L$ promoter, ADH, PH05, GPD, PGK and AOX1 promoters for yeast, a promoter derived from nucleopolyhedrovirus for silkworm cells and the like.

The selection markers which can be used include the kanamycin resistant gene, ampicilline resistant gene, tetracycline resistant gene and the like for *E. coli* vectors, the Leu2, Trp1, Ura3 and the like genes for yeast vectors, and the neomycin resistant gene, hygromycin resistant gene, thymidine kinase gene, dihydrofolate reductase gene and the like for mammalian cells. For inducible expression of the fusion as described above, a promoter capable of inducing the expression of downstream genes should be used.

DNA can be cloned into a vector by any method. The vector preferably contains either a poly-linker in which various restriction enzyme sites are present or a single restriction enzyme site. A particular restriction site in the vector can be cleaved with a restriction enzyme and a DNA can be inserted into the cleaved site. The expression vector containing the fusion gene of the present invention can be introduced into appropriate host cells to express and produce the protein encoded by the fusion gene described above.

The host cells include *E. coli* cells such as HB101, DH5, TG1, JM109, XL1-blue, BL21 (DE3), BL21 (DE3) pLysS and the like, bacterial cells such as and *Bacillus subtilis* and the like, fungal cells such as *Streptomyces, Aspergillus* and the like, yeast cells such as baker's yeast, methylotrophic yeast and the like, insects cells such as *Drosophila* S2, *Spodoptera* Sf9 and the like, mammalian cells such as CHO, COS, BHK, 3T3, C127 and the like. As described above, the cells resistant to the cell death-inducing protein included in the cell death-inducing fusion protein of the present invention, can also be used as a host.

Introduction of DNA into a host cell can be carried out by the conventional method using calcium chloride, calcium phosphate or DEAE dextran, electroporation and the like.

The recombinant fusion protein thus produced in host cells can be purified by various protein purification methods. For example, ammonium sulfate precipitation, gel filtration, ion-exchange chromatography, affinity chromatography and the like may be used singly or in appropriate combinations. When the product is expressed as a fusion protein with GST and the like, the product can be purified based on the nature of the fusion protein or the peptide fused to the target protein. For example, a protein expressed as a fusion protein with an amino acid sequence containing 6 consecutive histidine residues or more (i.e. histidine tag) can be purified using a chelate column because protein having histidine tag binds to the chelate column. A protein expressed as a fusion protein with GST can be purified efficiently using an affinity column in which glutathione is coupled to a carrier because GST has an affinity to glutathione.

The product thus produced is a fusion protein of a homing signal peptide, GFP and ΔNBax in this order from the N-terminus. The amino acid sequence of the fusion protein, in which the homing signal peptide is RGD and ΔNBax is the peptide from the residue 112 to residue 192 of human Bax protein, is shown in SEQ ID NO: 4. SEQ ID NO: 6 shows the amino acid sequence of the fusion protein in which the homing signal peptide is NGR and ΔNBax is the peptide from residue 112 to residue 192 of human Bax protein.

The fusion proteins in the present invention may have mutations such as deletion, substitution or addition of at least 1, preferably one or a few amino acids in these amino acid sequences, as long as they bind to endothelial cells undergoing angiogenesis and have stronger cell death-inducing activity than that of ΔNBax alone.

For example, at least one, preferably one or a few (for example, 1 to 10, more preferably 1 to 5) amino acids in the amino acid sequence shown in SEQ ID NO: 4 or SEQ ID NO: 6 may be deleted, or at least one, preferably one or a few (for example, 1 to 10, more preferably 1 to 5) amino acids in the amino acid sequence shown in SEQ ID NO: 4 or SEQ ID NO: 6 may be added, or at least one, preferably one or a few (for example, 1 to 10, more preferably 1 to 5) amino acids in the amino acid sequence shown in SEQ ID NO: 4 or SEQ ID NO: 6 may be substituted with other amino acids. The deletion, addition and substitution of amino acids may occur in any part of the homing signal peptide, GFP, or ΔNBax protein of the fusion protein.

Also included in the present invention is proteins which have homology to the amino acid sequence described above of at least 85% or above, preferably 90% or above, more preferably 95% or above and especially preferably 97% or above when calculated by BLAST or the like (for example, using the parameters of the initial setting which is a default setting).

A fusion protein using a homing signal peptide other than RGD and NGR may be included as the fusion protein of the present invention, even with deletion, addition and substitution in part of the amino acid sequence as described above, as long as its homing signal peptide binds to the target cells and it has enhanced cell death-inducing activity.

The present invention also includes a composition for cancer cell growth inhibitor containing the fusion protein described above as an active ingredient. This composition can be administered in various forms. The administration forms include oral formulation such as tablets, capsules, granules, powder, syrup and the like, or non-oral formulation such as injections, drip infusions, suppositories and the like. The cancer cell growth inhibitor of the present invention may also be administered to the cancer tissue directly. This cancer cell growth inhibitor is produced by known art and contains a carrier, diluent and excipient, which are normally used in pharmaceutical formulations. For example, lactose, magnesium stearate and the like are used as the carrier and excipient for tablets. The injections are prepared by dissolving, suspending or emulsifying the fusion protein in a sterile aqueous or oil based liquid normally used for injection. The aqueous solution for injection includes physiological saline, isotonic solution containing glucose or other supplements, and the like, and an appropriate solubilizer, for example, alcohol, polyalcohol such as propylene glycol, and non-ionic detergents may be used in combination. Oil based liquid includes sesame oil and soybean oil and the like, and benzylbenzoic acid, benzyl alcohol and the like as a solubilizer may be used in combination. Since the dosage is dependent of the symptoms, age, body weight and administration rout, it should be determined according to the judgment of the attending physician and the condition of the patient. Effective dosage may be obtained through in vitro tests or in vivo animal model test systems. For example, in mice bearing tumor, the volume of tumor is decreased by administering the fusion protein of the present invention at 50 µl of 500 µg/µL solution twice directly to the tumor of 0.2-0.4 cm$^3$ size.

The present invention is explained concretely by following examples but the present invention is not limited by these examples.

EXAMPLE 1

Construction of GFP-ΔNBax (1) Construction of GFP-ΔNBax

The GFP (Green Fluorescent Protein) gene (DNA fragment A) and the ΔNBax gene (DNA fragment B) were linked by the two-step PCR method.

DNA fragment A was amplified using a 5'-end primer (Primer 1) and 3'-end primer (Primer 2) and pGreenlantern (Invitrogen LifeTechnology) as a template. The 3'-half of Primer 1 contains the nucleotide sequence of the sense strand from the initiation codon of the GFP gene, and there is a restriction site (ATCGAT) of restriction enzyme ClaI at the 5'-end of the primer. The 5'-half of Primer 2 contains the anti-sense sequence of the 5'-end of the ΔNBax gene (from Ala 112 to Ser 118) and is complementary to Primer 3. Also, the 3'-half of the primer has an anti-sense nucleotide sequence of the 3'-end of the GFP gene except the termination codon.

DNA fragment B was amplified using a combination of Primer 3 and Primer 4 and pEF1BOS-Bax (Biochem Biophys Res Commun. 1998 Feb. 13; 243 (2):609-616) as a template. The 5'-end primer, Primer 3, is the sense nucleotide sequence of the 5'-end of the ΔNBax gene (coding for amino acid residue from Ala 112 to Ser 118 of Bax). The 3'-end primer, Primer 4, is the anti-sense sequence of the 3'-end of the ΔNBax gene (the 3'-end of Bax) containing the termination codon, and there is a restriction site (TCTAGA) of restriction enzyme Xba I at the 5'-end of the primer.

Detail of the PCR reaction is as follows.

Reaction mixture (volume 100 µl): 10 mM Tris-HCl, pH 8.3, 50 mM KCl, 1.5 mM MgCl$_2$, 0.001% gelatin, 0.2 mM each dATP, dCTP, dTTP, dGTP AmpliTaqGold: 2.5 U Pair of primers: a combination of Primer 1 and Primer 2, or a combination or Primer 3 and Primer 4 (each primer 1 µM)

Template DNA: 100 ng

Reaction condition 1: 94° C./10 min; (94° C./30 sec; 54° C./30 sec; 72° C./1 min)×15 cycles; 72° C./3 min After the reaction, the two amplified DNA fragments (A, B) were purified by 5% polyacrylamide gel electrophoresis. Next, the DNA fragments A and B (each 50 ng) were combined and mixed with the PCR reaction mixture described above (25 µl) to synthesize each complementary strand using AmpliTaqGold. The condition of the synthesis was following Reaction condition 2.

Reaction condition 2: 94° C./10 min; (94° C./30 sec; 36° C.-42° C./30 sec; 72° C./1 min)×5 cycles; 72° C./3 min After the reaction, 75 µl of the PCR reaction mixture containing Primer 1 and Primer 4 (final concentration 1 µM each), and AmpliTaqGold (2.5 U) was added, and the PCR reaction was carried out by following Reaction condition 3.

Reaction condition 3: 94° C./10 min; (94° C./30 sec; 54° C./30 sec; 72° C./1 min)×12 cycles; 72° C./3 min The 960-bp PCR product was purified by 5% polyacrylamide gel electrophoresis and cleaved with restriction enzymes, ClaI and XbaI. The fragment was cloned at the ClaI and XbaI restriction sites of the mammalian cell expression vector pEF-LACAB to obtain pEF-LACAB/GFP-ΔNBax.

(2) Comparison of Cell Death-Inducing Activity Between GFP-ΔNBax and ΔNBax.

The vector pEF-LAC was used to express ΔNBax and GFP-ΔNBax in mammalian cells (Edamatsu, H., Kaziro, Y., Itoh, H. Inducible high-level expression vector for mammalian cells, pEF-LAC carrying human elongation factor 1 alpha promoter and lac operator. Gene (1977) 187: 289-294). A DNA fragment, in which the initiation codon ATG was attached to the 5'-end of the nucleotide sequence coding ΔNBax (from nucleotide 754 to nucleotide 999 of SEQ ID NO: 3), was inserted into the multiple cloning sites (the XbaI restriction site) located at the downstream of the EF1α promoter of pEF-LAC to construct pEF-LAC-ΔNBax. As a control, plasmid pEF-LAC was used.

Similarly, another DNA fragment which contained the nucleotide sequence coding GFP-ΔNBax (from nucleotide 40 to nucleotide 999 of SEQ ID NO: 3) was cloned into the multiple cloning sites (between the ClaI restriction site and the XbaI restriction site) located at the downstream of the EF1α promoter of pEF-LAC to construct pEF-LAC-GFPΔ-NBax.

The cell death-inducing activity was measured by introducing the plasmid DNA described above into Jurkat cells to count by flow cytometry the number of surviving cells in which the gene was introduced. The number of surviving cells transfected with the plasmid DNA described above was compared with that of cells in which the control plasmid is introduced.

Jurkat cells were co-transfected with pEF-LAC-ΔNBax 2 µg and GFP expression plasmid, pGreenLantern (Invitrogen Life Technologies), 1 µg using SuperFect transfection kit (Qiagen). The method described in the manual of the kit was used. As a control, the mixture solution of pEF-LAC (empty vector) 2 µg and pGreenLantern 1 µg was similarly co-transfected into Jurkat cells. Since added amount of pGreenLantern is less than that of pEF-LAC-ΔNBax or pEF-LAC, the cells that pGreenLantern is introduced into, should be transfected with pEF-LAC-ΔNBax or pEF-LAC. Jurkat cells were transfected with 2 µg of pEF-LAC-GFPΔNBax using SuperFect transfection kit by the similar method described above. The living transfected cells emit green fluorescent light.

After the transfection, cells were cultured in RPMI1640 medium (Invitrogen Life Technologies) containing 10% FBS in 5% CO$_2$/95% Air, at 37° C. (BIO-LABO Juji Field Inc.) for 2 days and analyzed by flow cytometry (COULTER Co. EPICS ELITE ESP). Fifty thousand cells of normal size were selected (gated) by forward scattering (FS) and side scattering (SS), among which the number of cells emitting green fluorescent light (Em. 488 nm) of GFP was counted.

Result is shown in FIG. 1, in which the number of living cells in control pEF-LAC is given as 100. The number of living cells transfected with the GFPΔNBax gene was markedly smaller than that of living cells transfected with the ΔNBax gene, confirming that the cell death-inducing activity of GFPΔNBax is enhanced.

EXAMPLE 2

Construction of RGD-GFP-ΔNBax and NGR-GFP-ΔNBax

To link a homing signal sequence specific to endothelial cells (RGD and NGR) to the 5'-end of the GFP-ΔNBax fusion gene, an *E. coli* expression vector, pPROEX1 (Invitrogen Life Technology), was used. The vector pEF-LACAB and the GFP gene (nucleotide 166) in the GFP-ΔNBax fusion gene have 3 and 1 NcoI restriction sites, respectively. pEF-LACAB/GFP-ΔNBax was cleaved into 4 DNA fragments by NcoI, and the DNA fragment with about 1.3 kb long, which contains the 794-bp-long 3'-region (NcoI-XbaI) of the GFP-ΔNBax fusion gene (total length 980 bp), was cloned at the NcoI site of pPROEX1 in the right orientation to obtain pPROEX1/ΔNGFP-ΔNBax. Two NotI restriction sites are present in the sequence derived from pEF-LACAB (7 bp downstream of the XbaI site) and in the sequence of the vector pROEX1 at the downstream of 3'-end of cloned fragment (the NcoI site at the 3'-end). pPROEX1/ΔNGFP-ΔNBax is cleaved with Not I to remove the sequence derived from pEF-LACAB including the NcoI site at the 3'-end. The resultant plasmid pPROEX1/ΔNGFP-ΔNBax/ΔNotI was obtained.

Each homing signal peptide, RGD and NGR, was linked to the N-terminus of ΔNGFP-ΔNBax by the PCR method. Primer 5 contains the NcoI restriction site at the 5'-end, the nucleotide sequence coding for the homing signal peptide RGD and the nucleotide sequence of the 5'-end of the GFP gene at the 3'-end. Primer 5 and pEF-LACAB/GFP-ΔNBax (each 20 ng) were mixed with the PCR reaction mixture (25 µl) described above, and the complementary strand of Primer 5 was synthesized using AmpliTaqGold. The condition for the synthesis was the reaction condition 4 described below.

Reaction condition 4: 94° C./10 min; (94° C./30 sec; 44° C.-50° C./30 sec; 72° C./1 min)×6 cycles.

After the reaction, 75 µl of the PCR reaction mixture containing Primer 6 and Primer 7 (final concentration 1 µM each) and AmpliTaqGold (2.5 U) was added and PCR was carried out under the condition 5 described below.

Reaction condition 5: 94° C./10 min; (94° C./30 sec; 50° C./30 sec; 72° C./1 min)×16 cycles.

Primer 6 contains the nucleotide sequence of the 5'-half of Primer 5, and Primer 7 has the anti-sense nucleotide sequence of the GFP gene from nucleotide 200 to nucleotide 217. The PCR product was purified by 5% polyacrylamide gel electrophoresis and cleaved with restriction enzyme NcoI. This fragment was cloned to NcoI-cleaved pPROEX1/ΔNGFP-ΔNBax/ΔNotI to obtain pPROEX1/RGD-GFP-ΔNBax/ΔNotI. From this plasmid, GFP-ΔNBax carrying the homing signal peptide RGD at the N-terminus, RGD-GFP-ΔNBax, is produced. The nucleotide sequence was confirmed by DNA sequencing.

Primer 8 contains the NcoI restriction site at the 5'-end, the nucleotide sequence coding the homing signal peptide NGR and the 5'-end of the GFP gene at the 3'-end. The complementary strand of Primer 8 was synthesized by mixing Primer 8 and pEF-LACAB/GFP-ΔNBax (20 ng each) with the PCR reaction mixture described above and using AmpliTaqGold. The synthetic condition was the same as the reaction condition 4. After the reaction, 75 µl of the PCR reaction mixture containing Primer 9 and Primer 7 (final concentration 1 µM each) and AmpliTaqGold (2.5 U) was added and PCR was carried out under the reaction condition 5 described above. Primer 9 has a nucleotide sequence of the 5'-half of Primer 8. The PCR product was purified by 5% polyacrylamide gel electrophoresis and cleaved with restriction enzyme NcoI. This fragment was cloned to NcoI-cleaved pPROEX1/ ΔNGFP-ΔNBax/ΔNotI to obtain pPROEX1/NGR-GFP-ΔN-BaΔx/NotI. From this plasmid, GFP-ΔNBax carrying the homing signal peptide NGR at the N-terminus, NGR-GFP-ΔNBax, is produced. The nucleotide sequence was confirmed by DNA sequencing.

EXAMPLE 3

Subcloning of the RGD-GFP-ΔNBax Gene and the NGR-GFP-ΔNBax Gene into pIVEX2.2bNde and Production of these Gene Products in a Cell Free Protein Synthesis System To produce NGR-GFP-ΔNBax and RGD-GFP-ΔNBax in a cell free protein synthesis system, these genes were subcloned to a plasmid vector pIVEX2. 2bNde (Roche). The method for subcloning of the genes consisted of 2 steps using NcoI sites in the GFP gene as in Example 2.

pPROEX1/NGR-GFP-ΔNBax/NotI was cleaved with NcoI and XhoI, and a 822-bp DNA fragment containing the 794 bp-long 3'-region of the GFP-ΔNBax fusion gene (total length 960 bp) was recovered. This DNA fragment was cloned to the vector pIVEX2.2bNde cleaved with NcoI and XhoI beforehand to obtain pIVEX2. 2bNde/ΔNGFP-ΔNBax.

As in Example 2, the 206-bp NcoI DNA fragments of the NGR-GFP and RGD-GFP genes were amplified by the PCR method using pPROEX1/NGR-GFP-ΔNBax/ΔNotI and pPROEX1/RGD-GFP-ΔNBax/ΔNotI as templates, respectively. After recovering the DNA fragments, they were subcloned to NcoI-treated pIVEX2. 2bNde/ΔNGFP-ΔNBax to obtain pIVEX2.2bNde/NGR-GFP-ΔNBax and pIVEX2.2bNde/RGD-GFP-ΔNBax. By adding these plasmid DNAs to the RTS500HY kit reagent (Roche) according to the manual of Roche, RGD-GFP-ΔNBax protein and NGR-GFP-ΔNBax protein were synthesized using a cell system protein synthesis instrument, RTS Proteomaster (Roche). The synthesized proteins were confirmed and assayed (bovine serum albumin was used as the standard) by silver staining method using 2D Silver Staining Solution II (Daiichi Pure Chemicals Co.) and by conventional Coomassie Brilliant Blue staining method after SDS-PAGE electrophoresis using a PAG Mini gel (Daiichi Pure Chemicals Co.) stained.

(SEQ ID NO: 19)
Primer 5'-NNATCGATCCACCATGAGCAAGGGCGAG-3'
1.

(SEQ ID NO: 20)
Primer 5'-CTGGCAAAGTAGAAAAGGGCCTTGTACAGCTCGTC-3'
2.

(SEQ ID NO: 21)
Primer 5'-GCCCTTTTCTACTTTGCCAG-3'
3.

(SEQ ID NO: 22)
Primer 5'-NNTCTAGATCAGCCCATCTTCTTCCA-3'
4.

(SEQ ID NO: 23)
Primer 5'-CCATGGCCTGCGATTGCCGTGGTGATTGTTTTGTGGTGG
5.     TATGAGCAAGGGCGAGG-3'

(SEQ ID NO: 24)
Primer 5'-NNNNCCATGGCCTGCGATTGCC-3'
6.

(SEQ ID NO: 25)
Primer 5'-TGGAAAAGCACTGCACGC-3'
7.

(SEQ ID NO: 26)
Primer 5'-CCATGGCCTGCAACGGTCGTTGCGGTGGTATGAGCAAGG
8.     GCGAGG-3'

(SEQ ID NO: 27)
Primer 5'-NNNNCCATGGCCTGCAACGGTC-3'
9.

EXAMPLE 4

(1) Cell Culture.

HUVEC (human umbilical vein endothelial cell: Sanko Junyaku Co.) cells were used as cells undergoing angiogenesis and HeLa cells were used as control cells. EBM-2 (Sanko Junyaku Co.) and its supplement factors kit (including serum, antibiotics. Sanko Junyaku Co.) were used as the medium for HUVEC. HeLa cells were cultured in DMEM/F12 (Invitrogen LifeTechnology) supplemented with 10% FBS (fetal bovine serum; Sanko Junyaku Co.) and 1% penicillin-streptomycin (LifeTechnology).

(2) Introduction of Protein and Measurement of Cell Death-Inducing Activity.

HUVEC cells ($1.0 \times 10^3$ cells/well) and HeLa cells ($5.0 \times 10^2$ cells/well) were plated in a 96 well plate. Two hundred μl of medium per well was added. NGR-GFP-ΔNBax was produced by RTS500HY kit (Roche). The synthetic reaction mixture 20 μl was centrifuged (12,000 rpm, 4° C., 10 minutes). After removing the supernatant, the precipitant was re-dissolved in 20 μl of a dissolving solution (6M UREA, 0.15M NaCl, 20 mM Hepes pH7.2). After standing at room temperature for 10 min, the solution was centrifuged (12,000 rpm, 4° C., 10 minutes), and the supernatant was used as the sample of NGR-GFP-ΔNBax. The concentration of NGR-GFP-ΔNBax protein was determined to be 150 ng/μl by staining with coomassie brilliant blue (CBB) after conventional SDS-PAGE, using bovine serum albumin of known concentration as the standard. One hundred and fifty μl of the cell culture medium removed from the well was mixed with NGR-GFT-ΔNBax, the amount of which is shown below, and then returned to the well. After 24 and 48 hours of the addition of the protein, PI and Hoechest 33342 were added to the medium at 5 μM to determine the cytotoxicity. The numbers of PI positive cells and Hoechest positive cells were counted under a fluorescent microscope (LEICA DMIRB). A total of 1000 cells were counted in each well in 6 fields (100×field) not overlapping each other.

Two experiments were carried out. In Experiment 1, only HUVEC cells were used. HUVEC cells were treated with NGR-GFP-ΔNBax (750 ng), or treated with the same volume (5 μl) of the dissolving solution (6M UREA, 0.15 M NaCl, 20 mM Hepes pH 7.2) as control. Results were evaluated after 48 hours. In Experiment 2, HUVEC cells and HeLa cells were used and NGR-GFP-ΔNBax (200 ng and 60 ng) was added to both cells, and results were evaluated after 24 hours. Table 1 shows the results. As shown in Table 1, cell death (PI positive rate) after 48 hours occurred more frequently in HUVEC cells treated with NGR-GFP-ΔNBax fusion protein than in the control to which only the solvent of an equal volume was added, where HUVEC cells are the model of endothelial cells undergoing angiogenesis. Also, when NGR-GFP-ΔNBax fusion protein was added to HUVEC cells, the cell death ratio after 24 hours was 4 to more than 10 times higher than that of HeLa cells treated with NGR-GFP-ΔNBax fusion protein, where HeLa cells don't undergo angiogenesis.

TABLE 1

| Experiment 1 | Cell Death (PI positive ratio) after 48 hours | | |
|---|---|---|---|
| | NGR-GFP-ΔNBax | Control (solvent only added) | No addition |
| HUVEC | 42.4% | 11.9% | 8.5% |

| | Cell Death (PI positive ratio) after 24 hours | | |
|---|---|---|---|
| | NGR-GFP-ΔNBax | | |
| Experiment 2 | 200 ng | 60 ng | No addition |
| HUVEC cell | 13.1% | 5.4% | 1.4% |
| HeLa cell | 3.2% | 0.4% | 0.4% |

Note:
"No addition" means PI positive ratio of cells in the normal medium without any extra addition nor any extra treatment.

Figure 2:
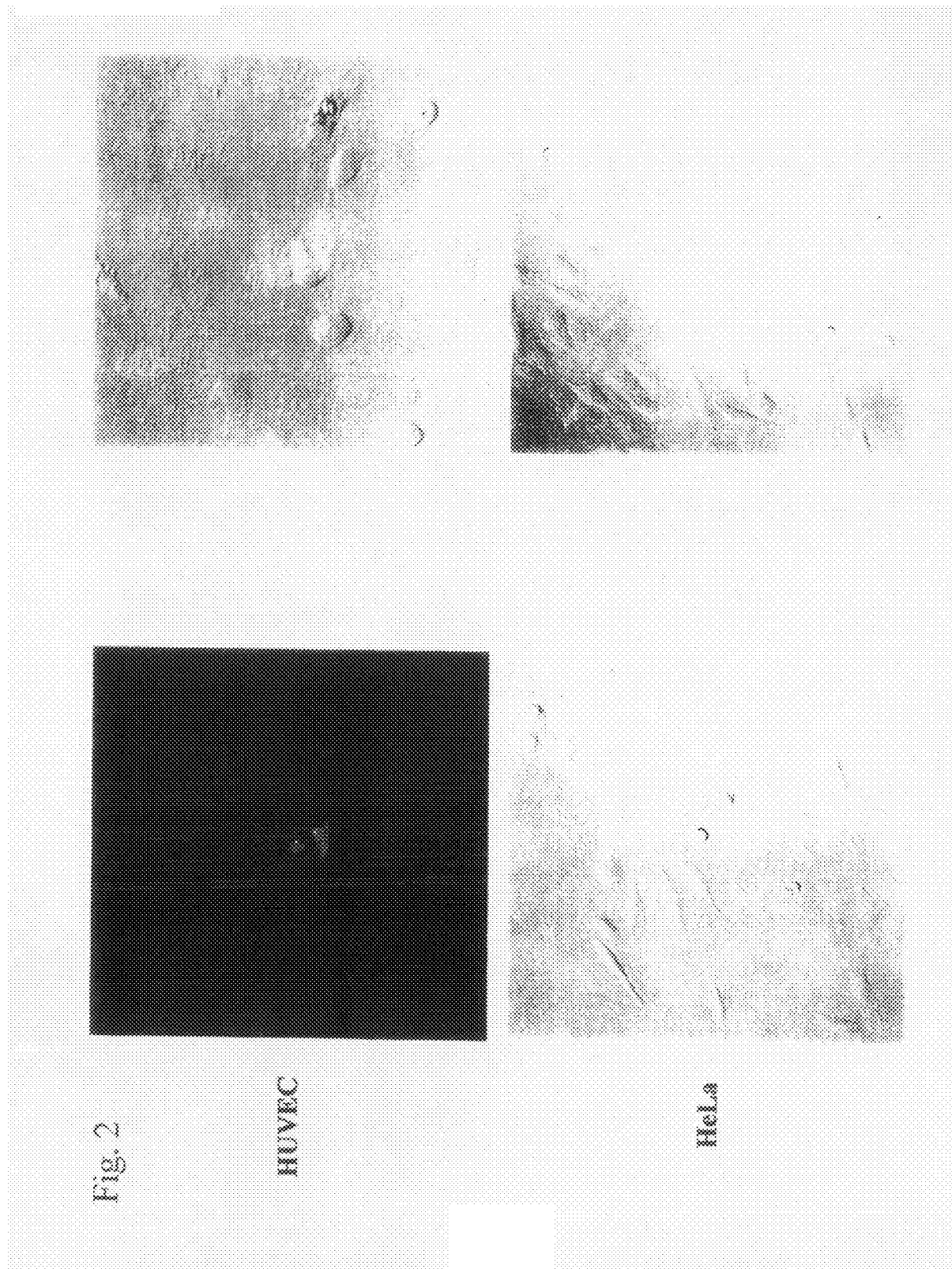
FIG. 2 is a photograph showing the incorporation of NGR-GFP-ΔNBax into a cell.
Figure 3:
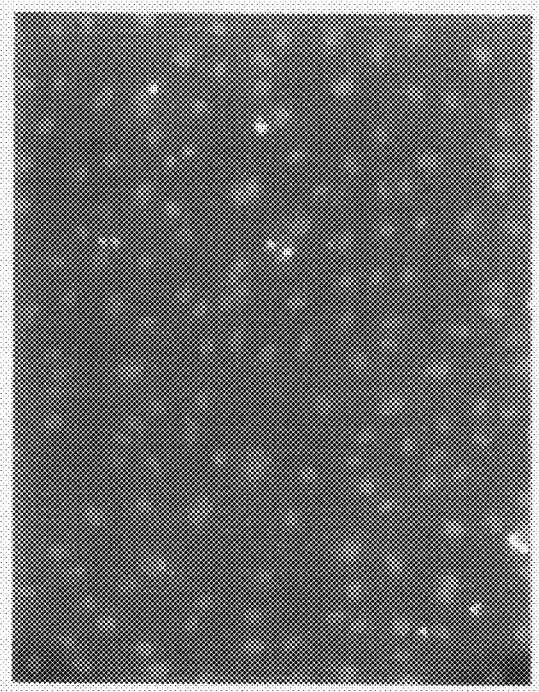
FIG. 3 is a photograph showing an image of PI positive cells.
Figure 3:
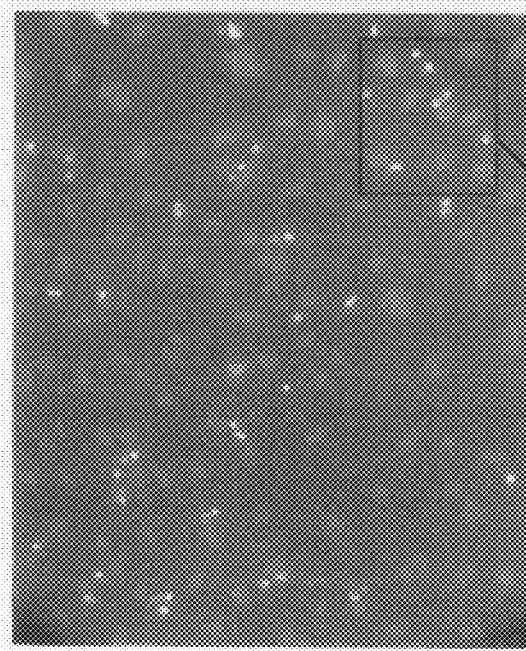
Figure 3:
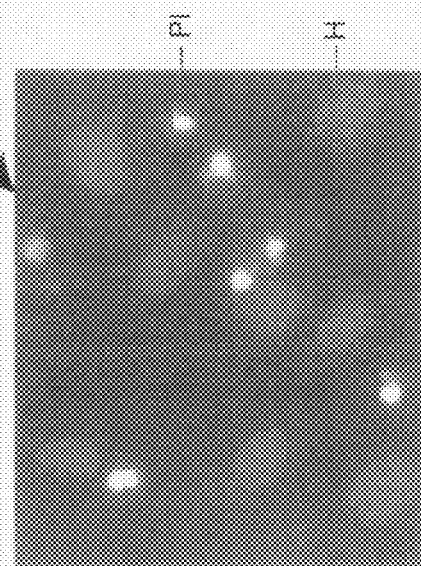

To confirm that RGD-GFP-ΔNBax protein and NGR-GFP-ΔNBax protein are introduced into the cells, $1\times10^5$ HUVEC cells and $5\times10^4$ HeLa cells were plated in each well of a 4-well plate (Sonic Seal Slide; LAB-TEK Co.). Two hundred ng of NGR-GFP-ΔNBax fusion protein was added to each well. After 3 hours, medium was changed and PI (5 μM) was added. Fluorescence of GFP and PI was observed using a Confocal Laser Scanning Microscope (FLUOVIEWFV300 OLYMPUS) (with 10× objective lens). FIG. 2 shows the presence of GFP inside the cells. While HUVEC cells undergoing cell death were shown to emit the fluorescence of GFP inside the cells (the nuclei of dead cells appear red), no fluorescence was observed in HeLa cells, indicating that the fusion protein was incorporated into only HUVEC cells, which were the model of endothelial cells undergoing angiogenesis, by the action of a homing signal peptide, NGR. FIG. 3 shows cells stained with PI. The left figure shows HUVEC cells treated with NGR-GFP-ΔNBax fusion protein, and the right figure shows HeLa cells treated with NGR-GFP-ΔNBax fusion protein. These figures indicate that the number of PI positive HUVEC cells is higher than that of PI-positive HeLa cells. Below FIG. 3, the enlarged view of HUVEC cells treated with NGR-GFP-ΔNBax protein inside the box in the left image of FIG. 3 is shown. In this enlarged view, the cell indicated with PI (PI positive cells) is dead and the cell indicated with H (Hoechst positive cells) is living.

EXAMPLE 5

Anti-Tumor Effect of NGR-GFP-ΔNBax on Tumor-Bearing Mice

Figure 4:
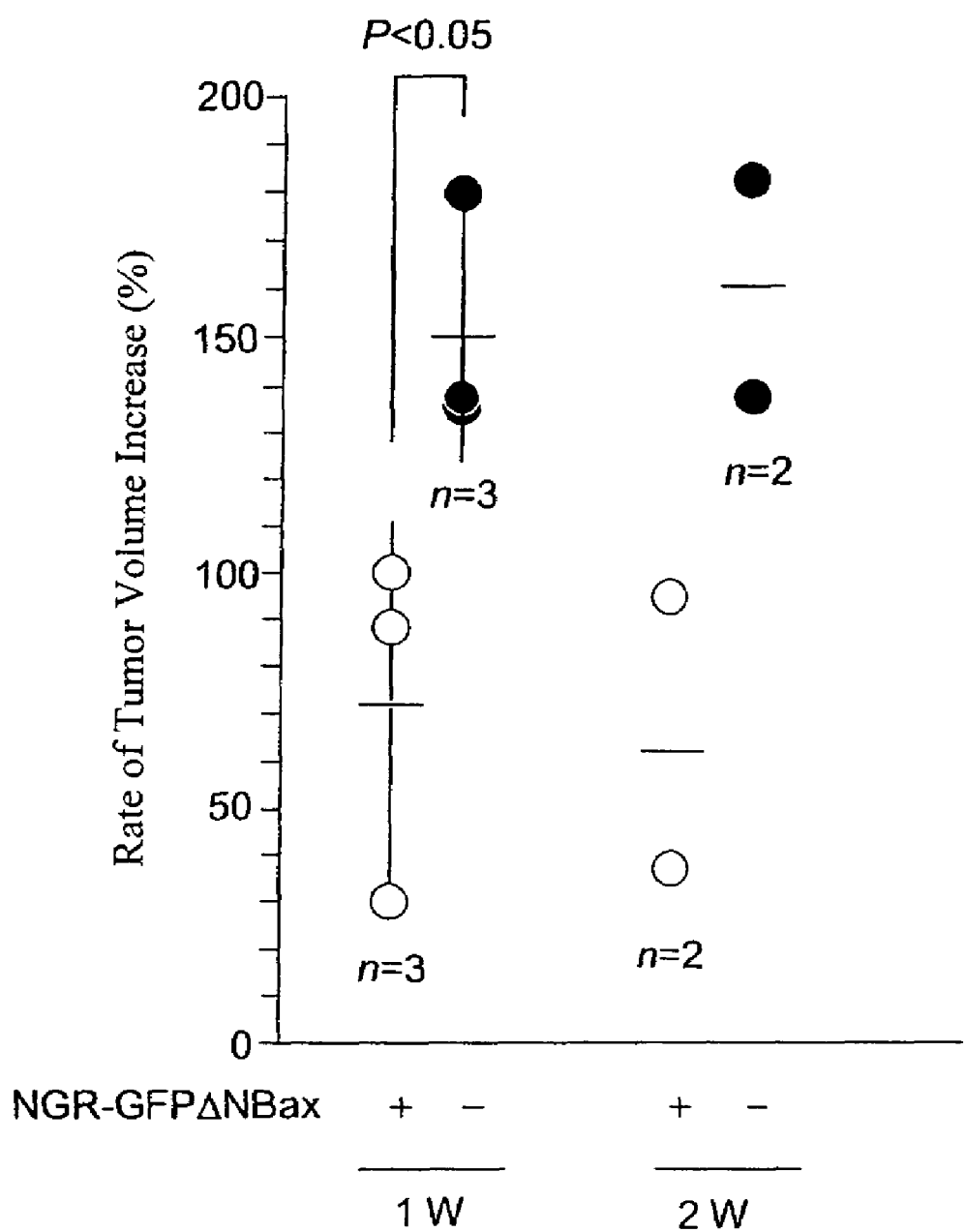
FIG. 4 shows anti-tumor effect of NGR-GFP-ΔNBax using a mouse bearing tumor.

Tumor-bearing mice were prepared by subcutaneously transplanting HeLa cells ($1\times10^7$ cells) to nude mice BALB/c-nu/nu Slc (female, 8 weeks old). The size of tumor (volume) was determined under anesthesia (Nembutal) by measuring the long and short diameters with a precision caliper and calculating using conventional equation (long diameter)×(short diameter)$^2$/2. NGR-GFP-ΔNBax was synthesized using RTSHY500 kit (Roche). The synthetic reaction mixture 100 μl was centrifuged (12,000 rpm, 4° C., 10 minutes). After removing the supernatant, the precipitant was re-dissolved in 100 μl of the dissolving solution (6M UREA, 0.15M NaCl, 20 mM Hepes pH7.2). After standing at room temperature for 10 min, the solution was centrifuged (12,000 rpm, 4° C., 10 minutes), and the supernatant was used as NGR-GFP-ΔNBax sample. The concentration of NGR-GFP-ΔNBax was determined to be 500 ng/μl by conventional SDS-PAGE followed by staining with coomassie brilliant blue (CBB) using bovine serum albumin of known concentration as the standard. NGR-GFP-ΔNBax 50 μl was injected twice directly to a tumor (0.2-0.4 cm$^3$) of the 3 tumor-bearing mice after the size of the tumors was measured under Nembutal anesthesia. As controls 3 tumor-bearing mice were injected with the dissolving solution (6M UREA, 0.15M NaCl, 20 mM Hepes pH7.2) only. After one week, the size of the tumor was measured (FIG. 4, 1 W; white circle, NGR-GFP-ΔNBax sample was administered; solid circle, control). Further, for each two mice, NGR-GFP-ΔNBax sample and the dissolving solution (6M UREA, 0.15M NaCl, 20 mM Hepes pH7.2) as control were injected twice each with 50 μl directly to the tumor in the same way as the first administration, and after one week the size of the tumors was measured (FIG. 4, 2 W). In the figure, the rate of volume increase of each tumor (white circle, NGR-GFP-ΔNBax sample is administered; solid circle, control) is expressed as the percentage (%) of the tumor volume before the first injection, and the average (horizontal bar) is also shown. In the measurement after 1 week of the first injection, the standard deviations were shown with horizontal bars, and the statistical analysis by Student's t-test indicated statistical significance. The decrease of tumor volume by NGR-GFP-ΔNBax administration (once and twice) was observed.

INDUSTRIAL APPLICABILITY

As shown in the results of Example 4, the fusion protein, in which the homing signal peptide, GFP and ΔNBax are fused in this order, induced cell death specifically and potently in cells undergoing angiogenesis. This suggests that the fusion protein is specifically incorporated into cells undergoing angiogenesis by the action of the homing signal peptide in the fusion protein, and the cell death is induced by the action of ΔNBax in which the cell death-inducing activity is enhanced by GFP. Further, as shown in Example 5, the administration of the fusion protein, in which the homing signal peptide, GFP and ΔNBax are fused in this order, to tumor bearing mice caused the decrease in tumor volume. These results clearly indicate that the fusion protein of the present invention can induce, specifically and potently, the cell death of cancer cells undergoing angiogenesis and is useful as an inhibitor of cancer cell growth, that is an anti-cancer drug.

Table of Sequences Free Text
SEQ ID NO: 7-18: homing signal peptides
SEQ ID NO: 19-27: primers The whole contents of all the publications referred herein are hereby incorporated. It is to be understood that variations and modifications may be possible within the purview and the cope described in attached claims by those skilled in the art. It is intended that the present invention includes such variations and modifications.

The invention claimed is:

1. A fusion gene comprising a cell death-inducing gene that acts specifically on a surface receptor of endothelial cells undergoing angiogenesis, wherein the fusion gene is produced by fusing, a gene that codes for a homing signal peptide sequence specific for the surface receptor of endothelial cells undergoing angiogenesis, a gene coding for green fluorescent protein (GFP) and a gene coding for ΔNBax protein, which is human Bax with a deletion of the N-terminal sequence including the BH3 domain and has cell death inducing activity and comprises an amino acid sequence from the $112^{th}$ to the $192^{nd}$ of human Bax of the amino acid sequence of SEQ ID NO: 2, in this order.

2. The fusion gene according to claim 1, wherein the homing signal peptide sequence is NGR peptide sequence.

3. The fusion gene according to claim 1 or 2, wherein the fusion gene comprises following DNA of (p) or (q), (p) a DNA having a nucleotide sequence of SEQ ID NO: 3,
(q) a DNA which hybridizes with a DNA having a complete complementary sequence of the DNA of (p) under a stringent condition and which codes for a protein which binds to endothelial cells undergoing angiogenesis and which has an enhanced cell death-inducing activity.

4. An expression vector containing the fusion gene according to claim 1.

5. The expression vector according to claim 4, which can express the fusion gene in a cell-free system.

6. A method for producing the fusion protein encoded by the fusion gene according to claim 1, including a step of in vitro expression by an expression vector containing the fusion gene of claim 1, which can express the fusion gene in a cell-free system.

* * * * *

SEQUENCE LISTING

<160> NUMBER OF SEQ ID NOS: 27

<210> SEQ ID NO 1
<211> LENGTH: 579
<212> TYPE: DNA
<213> ORGANISM: Homo sapiens
<220> FEATURE:
<221> NAME/KEY: CDS
<222> LOCATION: (1)..(579)

<400> SEQUENCE: 1

```
atg gac ggg tcc ggg gag cag ccc aga ggc ggg ggg ccc acc agc tct      48
Met Asp Gly Ser Gly Glu Gln Pro Arg Gly Gly Gly Pro Thr Ser Ser
 1               5                  10                  15 gag cag atc atg aag aca ggg gcc ctt ttg ctt cag ggt ttc atc cag      96
Glu Gln Ile Met Lys Thr Gly Ala Leu Leu Leu Gln Gly Phe Ile Gln
             20                  25                  30 gat cga gca ggg cga atg ggg ggg gag gca ccc gag ctg gcc ctg gac     144
Asp Arg Ala Gly Arg Met Gly Gly Glu Ala Pro Glu Leu Ala Leu Asp
         35                  40                  45 ccg gtg cct cag gat gcg tcc acc aag aag ctg agc gag tgt ctc aag     192
Pro Val Pro Gln Asp Ala Ser Thr Lys Lys Leu Ser Glu Cys Leu Lys
     50                  55                  60 cgc atc ggg gac gaa ctg gac agt aac atg gag ctg cag agg atg att     240
Arg Ile Gly Asp Glu Leu Asp Ser Asn Met Glu Leu Gln Arg Met Ile
 65                  70                  75                  80 gcc gcc gtg gac aca gac tcc ccc cga gag gtc ttt ttc cga gtg gca     288
Ala Ala Val Asp Thr Asp Ser Pro Arg Glu Val Phe Phe Arg Val Ala
                 85                  90                  95 gct gac atg ttt tct gac ggc aac ttc aac tgg ggc cgg gtt gtc gcc     336
Ala Asp Met Phe Ser Asp Gly Asn Phe Asn Trp Gly Arg Val Val Ala
            100                 105                 110 ctt ttc tac ttt gcc agc aaa ctg gtg ctc aag gcc ctg tgc acc aag     384
Leu Phe Tyr Phe Ala Ser Lys Leu Val Leu Lys Ala Leu Cys Thr Lys
        115                 120                 125 gtg ccg gaa ctg atc aga acc atc atg ggc tgg aca ttg gac ttc ctc     432
Val Pro Glu Leu Ile Arg Thr Ile Met Gly Trp Thr Leu Asp Phe Leu
    130                 135                 140 cgg gag cgg ctg ttg ggc tgg atc caa gac cag ggt ggt tgg gac ggc     480
Arg Glu Arg Leu Leu Gly Trp Ile Gln Asp Gln Gly Gly Trp Asp Gly
145                 150                 155                 160 ctc ctc tcc tac ttt ggg acg ccc acg tgg cag acc gtg acc atc ttt     528
Leu Leu Ser Tyr Phe Gly Thr Pro Thr Trp Gln Thr Val Thr Ile Phe
                165                 170                 175 gtg gcg gga gtg ctc acc gcc tcg ctc acc atc tgg aag aag atg ggc     576
Val Ala Gly Val Leu Thr Ala Ser Leu Thr Ile Trp Lys Lys Met Gly
            180                 185                 190 tga                                                                  579
```

<210> SEQ ID NO 2
<211> LENGTH: 192
<212> TYPE: PRT
<213> ORGANISM: Homo sapiens

<400> SEQUENCE: 2

```
Met Asp Gly Ser Gly Glu Gln Pro Arg Gly Gly Gly Pro Thr Ser Ser
 1               5                  10                  15

Glu Gln Ile Met Lys Thr Gly Ala Leu Leu Leu Gln Gly Phe Ile Gln
             20                  25                  30
```

```
Asp Arg Ala Gly Arg Met Gly Gly Glu Ala Pro Glu Leu Ala Leu Asp
         35                  40                  45

Pro Val Pro Gln Asp Ala Ser Thr Lys Lys Leu Ser Glu Cys Leu Lys
 50                  55                  60

Arg Ile Gly Asp Glu Leu Asp Ser Asn Met Glu Leu Gln Arg Met Ile
 65                  70                  75                  80

Ala Ala Val Asp Thr Asp Ser Pro Arg Glu Val Phe Phe Arg Val Ala
                 85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

<210> SEQ ID NO 3
<211> LENGTH: 999
<212> TYPE: DNA
<213> ORGANISM: Homo sapiens
<220> FEATURE:
<221> NAME/KEY: CDS
<222> LOCATION: (1)..(999)

<400> SEQUENCE: 3 atg gcc tgc gat tgc cgt ggt gat tgt ttt tgt ggt ggt atg agc aag      48
Met Ala Cys Asp Cys Arg Gly Asp Cys Phe Cys Gly Gly Met Ser Lys
 1               5                  10                  15 ggc gag gaa ctg ttc act ggc gtg gtc cca att ctc gtg gaa ctg gat      96
Gly Glu Glu Leu Phe Thr Gly Val Val Pro Ile Leu Val Glu Leu Asp
                 20                  25                  30 ggc gat gtg aat ggg cac aaa ttt tct gtc agc gga gag ggt gaa ggt     144
Gly Asp Val Asn Gly His Lys Phe Ser Val Ser Gly Glu Gly Glu Gly
             35                  40                  45 gat gcc aca tac gga aag ctc acc ctg aaa ttc atc tgc acc act gga     192
Asp Ala Thr Tyr Gly Lys Leu Thr Leu Lys Phe Ile Cys Thr Thr Gly
 50                  55                  60 aag ctc cct gtg cca tgg cca aca ctg gtc act acc ttc acc tat ggc     240
Lys Leu Pro Val Pro Trp Pro Thr Leu Val Thr Thr Phe Thr Tyr Gly
 65                  70                  75                  80 gtg cag tgc ttt tcc aga tac cca gac cat atg aag cag cat gac ttt     288
Val Gln Cys Phe Ser Arg Tyr Pro Asp His Met Lys Gln His Asp Phe
                 85                  90                  95 ttc aag agc gcc atg ccc gag ggc tat gtg cag gag aga acc atc ttt     336
Phe Lys Ser Ala Met Pro Glu Gly Tyr Val Gln Glu Arg Thr Ile Phe
            100                 105                 110 ttc aaa gat gac ggg aac tac aag acc cgc gct gaa gtc aag ttc gaa     384
Phe Lys Asp Asp Gly Asn Tyr Lys Thr Arg Ala Glu Val Lys Phe Glu
        115                 120                 125 ggt gac acc ctg gtg aat aga atc gag ctg aag ggc att gac ttt aag     432
Gly Asp Thr Leu Val Asn Arg Ile Glu Leu Lys Gly Ile Asp Phe Lys
    130                 135                 140 gag gat gga aac att ctc ggc cac aag ctg gaa tac aac tat aac tcc     480
Glu Asp Gly Asn Ile Leu Gly His Lys Leu Glu Tyr Asn Tyr Asn Ser
```

```
                    145                 150                 155                 160
cac aat gtg tac atc atg gcc gac aag caa aag aat ggc atc aag gtc    528
His Asn Val Tyr Ile Met Ala Asp Lys Gln Lys Asn Gly Ile Lys Val
                165                 170                 175 aac ttc aag atc aga cac aac att gag gat gga tcc gtg cag ctg gcc    576
Asn Phe Lys Ile Arg His Asn Ile Glu Asp Gly Ser Val Gln Leu Ala
            180                 185                 190 gac cat tat caa cag aac act cca atc ggc gac ggc cct gtg ctc ctc    624
Asp His Tyr Gln Gln Asn Thr Pro Ile Gly Asp Gly Pro Val Leu Leu
        195                 200                 205 cca gac aac cat tac ctg tcc acc cag tct gcc ctg tct aaa gat ccc    672
Pro Asp Asn His Tyr Leu Ser Thr Gln Ser Ala Leu Ser Lys Asp Pro
    210                 215                 220 aac gaa aag aga gac cac atg gtc ctg ctg gag ttt gtg acc gct gct    720
Asn Glu Lys Arg Asp His Met Val Leu Leu Glu Phe Val Thr Ala Ala
225                 230                 235                 240 ggg atc aca cat ggc atg gac gag ctg tac aag gcc ctt ttc tac ttt    768
Gly Ile Thr His Gly Met Asp Glu Leu Tyr Lys Ala Leu Phe Tyr Phe
                245                 250                 255 gcc agc aaa ctg gtg ctc aag gcc ctg tgc acc aag gtg ccg gaa ctg    816
Ala Ser Lys Leu Val Leu Lys Ala Leu Cys Thr Lys Val Pro Glu Leu
            260                 265                 270 atc aga acc atc atg ggc tgg aca ttg gac ttc ctc cgg gag cgg ctg    864
Ile Arg Thr Ile Met Gly Trp Thr Leu Asp Phe Leu Arg Glu Arg Leu
        275                 280                 285 ttg ggc tgg atc caa gac cag ggt ggt tgg gac ggc ctc ctc tcc tac    912
Leu Gly Trp Ile Gln Asp Gln Gly Gly Trp Asp Gly Leu Leu Ser Tyr
    290                 295                 300 ttt ggg acg ccc acg tgg cag acc gtg acc atc ttt gtg gcg gga gtg    960
Phe Gly Thr Pro Thr Trp Gln Thr Val Thr Ile Phe Val Ala Gly Val
305                 310                 315                 320 ctc acc gcc tca ctc acc atc tgg aag aag atg ggc tga                999
Leu Thr Ala Ser Leu Thr Ile Trp Lys Lys Met Gly
                325                 330

<210> SEQ ID NO 4
<211> LENGTH: 332
<212> TYPE: PRT
<213> ORGANISM: Homo sapiens

<400> SEQUENCE: 4

Met Ala Cys Asp Cys Arg Gly Asp Cys Phe Cys Gly Gly Met Ser Lys
 1               5                  10                  15

Gly Glu Glu Leu Phe Thr Gly Val Val Pro Ile Leu Val Glu Leu Asp
                20                  25                  30

Gly Asp Val Asn Gly His Lys Phe Ser Val Ser Gly Glu Gly Glu Gly
            35                  40                  45

Asp Ala Thr Tyr Gly Lys Leu Thr Leu Lys Phe Ile Cys Thr Thr Gly
        50                  55                  60

Lys Leu Pro Val Pro Trp Pro Thr Leu Val Thr Thr Phe Thr Tyr Gly
 65                 70                  75                  80

Val Gln Cys Phe Ser Arg Tyr Pro Asp His Met Lys Gln His Asp Phe
                85                  90                  95

Phe Lys Ser Ala Met Pro Glu Gly Tyr Val Gln Glu Arg Thr Ile Phe
            100                 105                 110

Phe Lys Asp Asp Gly Asn Tyr Lys Thr Arg Ala Glu Val Lys Phe Glu
        115                 120                 125

Gly Asp Thr Leu Val Asn Arg Ile Glu Leu Lys Gly Ile Asp Phe Lys
```

-continued

```
            130                 135                 140
Glu Asp Gly Asn Ile Leu Gly His Lys Leu Glu Tyr Asn Tyr Asn Ser
145                 150                 155                 160

His Asn Val Tyr Ile Met Ala Asp Lys Gln Lys Asn Gly Ile Lys Val
                165                 170                 175

Asn Phe Lys Ile Arg His Asn Ile Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Ala Leu Ser Lys Asp Pro
210                 215                 220

Asn Glu Lys Arg Asp His Met Val Leu Leu Glu Phe Val Thr Ala Ala
225                 230                 235                 240

Gly Ile Thr His Gly Met Asp Glu Leu Tyr Lys Ala Leu Phe Tyr Phe
                245                 250                 255

Ala Ser Lys Leu Val Leu Lys Ala Leu Cys Thr Lys Val Pro Glu Leu
            260                 265                 270

Ile Arg Thr Ile Met Gly Trp Thr Leu Asp Phe Leu Arg Glu Arg Leu
        275                 280                 285

Leu Gly Trp Ile Gln Asp Gln Gly Gly Trp Asp Gly Leu Leu Ser Tyr
290                 295                 300

Phe Gly Thr Pro Thr Trp Gln Thr Val Thr Ile Phe Val Ala Gly Val
305                 310                 315                 320

Leu Thr Ala Ser Leu Thr Ile Trp Lys Lys Met Gly
                325                 330

<210> SEQ ID NO 5
<211> LENGTH: 987
<212> TYPE: DNA
<213> ORGANISM: Homo sapiens
<220> FEATURE:
<221> NAME/KEY: CDS
<222> LOCATION: (1)..(987)

<400> SEQUENCE: 5 atg gcc tgc aac ggt cgt tgc ggt ggt atg agc aag ggc gag gaa ctg        48
Met Ala Cys Asn Gly Arg Cys Gly Gly Met Ser Lys Gly Glu Glu Leu
 1               5                  10                  15 ttc act ggc gtg gtc cca att ctc gtg gaa ctg gat ggc gat gtg aat        96
Phe Thr Gly Val Val Pro Ile Leu Val Glu Leu Asp Gly Asp Val Asn
             20                  25                  30 ggg cac aaa ttt tct gtc agc gga gag ggt gaa ggt gat gcc aca tac       144
Gly His Lys Phe Ser Val Ser Gly Glu Gly Glu Gly Asp Ala Thr Tyr
         35                  40                  45 gga aag ctc acc ctg aaa ttc atc tgc acc act gga aag ctc cct gtg       192
Gly Lys Leu Thr Leu Lys Phe Ile Cys Thr Thr Gly Lys Leu Pro Val
     50                  55                  60 cca tgg cca aca ctg gtc act acc ttc acc tat ggc gtg cag tgc ttt       240
Pro Trp Pro Thr Leu Val Thr Thr Phe Thr Tyr Gly Val Gln Cys Phe
 65                  70                  75                  80 tcc aga tac cca gac cat atg aag cag cat gac ttt ttc aag agc gcc       288
Ser Arg Tyr Pro Asp His Met Lys Gln His Asp Phe Phe Lys Ser Ala
                 85                  90                  95 atg ccc gag ggc tat gtg cag gag aga acc atc ttt ttc aaa gat gac       336
Met Pro Glu Gly Tyr Val Gln Glu Arg Thr Ile Phe Phe Lys Asp Asp
            100                 105                 110 ggg aac tac aag acc cgc gct gaa gtc aag ttc gaa ggt gac acc ctg       384
Gly Asn Tyr Lys Thr Arg Ala Glu Val Lys Phe Glu Gly Asp Thr Leu
```

-continued

```
                      115                 120                 125
gtg aat aga atc gag ctg aag ggc att gac ttt aag gag gat gga aac    432
Val Asn Arg Ile Glu Leu Lys Gly Ile Asp Phe Lys Glu Asp Gly Asn
    130                 135                 140 att ctc ggc cac aag ctg gaa tac aac tat aac tcc cac aat gtg tac    480
Ile Leu Gly His Lys Leu Glu Tyr Asn Tyr Asn Ser His Asn Val Tyr
145                 150                 155                 160 atc atg gcc gac aag caa aag aat ggc atc aag gtc aac ttc aag atc    528
Ile Met Ala Asp Lys Gln Lys Asn Gly Ile Lys Val Asn Phe Lys Ile
                165                 170                 175 aga cac aac att gag gat gga tcc gtg cag ctg gcc gac cat tat caa    576
Arg His Asn Ile Glu Asp Gly Ser Val Gln Leu Ala Asp His Tyr Gln
            180                 185                 190 cag aac act cca atc ggc gac ggc cct gtg ctc ctc cca gac aac cat    624
Gln Asn Thr Pro Ile Gly Asp Gly Pro Val Leu Leu Pro Asp Asn His
        195                 200                 205 tac ctg tcc acc cag tct gcc ctg tct aaa gat ccc aac gaa aag aga    672
Tyr Leu Ser Thr Gln Ser Ala Leu Ser Lys Asp Pro Asn Glu Lys Arg
210                 215                 220 gac cac atg gtc ctg ctg gag ttt gtg acc gct gct ggg atc aca cat    720
Asp His Met Val Leu Leu Glu Phe Val Thr Ala Ala Gly Ile Thr His
225                 230                 235                 240 ggc atg gac gag ctg tac aag gcc ctt ttc tac ttt gcc agc aaa ctg    768
Gly Met Asp Glu Leu Tyr Lys Ala Leu Phe Tyr Phe Ala Ser Lys Leu
                245                 250                 255 gtg ctc aag gcc ctg tgc acc aag gtg ccg gaa ctg atc aga acc atc    816
Val Leu Lys Ala Leu Cys Thr Lys Val Pro Glu Leu Ile Arg Thr Ile
            260                 265                 270 atg ggc tgg aca ttg gac ttc ctc cgg gag cgg ctg ttg ggc tgg atc    864
Met Gly Trp Thr Leu Asp Phe Leu Arg Glu Arg Leu Leu Gly Trp Ile
        275                 280                 285 caa gac cag ggt ggt tgg gac ggc ctc ctc tcc tac ttt ggg acg ccc    912
Gln Asp Gln Gly Gly Trp Asp Gly Leu Leu Ser Tyr Phe Gly Thr Pro
    290                 295                 300 acg tgg cag acc gtg acc atc ttt gtg gcg gga gtg ctc acc gcc tca    960
Thr Trp Gln Thr Val Thr Ile Phe Val Ala Gly Val Leu Thr Ala Ser
305                 310                 315                 320 ctc acc atc tgg aag aag atg ggc tga                                987
Leu Thr Ile Trp Lys Lys Met Gly
                325
```

<210> SEQ ID NO 6
<211> LENGTH: 328
<212> TYPE: PRT
<213> ORGANISM: Homo sapiens

<400> SEQUENCE: 6

```
Met Ala Cys Asn Gly Arg Cys Gly Gly Met Ser Lys Gly Glu Glu Leu
1               5                   10                  15

Phe Thr Gly Val Val Pro Ile Leu Val Glu Leu Asp Gly Asp Val Asn
                20                  25                  30

Gly His Lys Phe Ser Val Ser Gly Glu Gly Glu Gly Asp Ala Thr Tyr
            35                  40                  45

Gly Lys Leu Thr Leu Lys Phe Ile Cys Thr Thr Gly Lys Leu Pro Val
        50                  55                  60

Pro Trp Pro Thr Leu Val Thr Thr Phe Thr Tyr Gly Val Gln Cys Phe
65                  70                  75                  80

Ser Arg Tyr Pro Asp His Met Lys Gln His Asp Phe Phe Lys Ser Ala
                85                  90                  95
```

-continued

```
Met Pro Glu Gly Tyr Val Gln Glu Arg Thr Ile Phe Phe Lys Asp Asp
            100                 105                 110

Gly Asn Tyr Lys Thr Arg Ala Glu Val Lys Phe Glu Gly Asp Thr Leu
        115                 120                 125

Val Asn Arg Ile Glu Leu Lys Gly Ile Asp Phe Lys Glu Asp Gly Asn
    130                 135                 140

Ile Leu Gly His Lys Leu Glu Tyr Asn Tyr Asn Ser His Asn Val Tyr
145                 150                 155                 160

Ile Met Ala Asp Lys Gln Lys Asn Gly Ile Lys Val Asn Phe Lys Ile
                165                 170                 175

Arg His Asn Ile Glu Asp Gly Ser Val Gln Leu Ala Asp His Tyr Gln
            180                 185                 190

Gln Asn Thr Pro Ile Gly Asp Gly Pro Val Leu Leu Pro Asp Asn His
        195                 200                 205

Tyr Leu Ser Thr Gln Ser Ala Leu Ser Lys Asp Pro Asn Glu Lys Arg
    210                 215                 220

Asp His Met Val Leu Leu Glu Phe Val Thr Ala Ala Gly Ile Thr His
225                 230                 235                 240

Gly Met Asp Glu Leu Tyr Lys Ala Leu Phe Tyr Phe Ala Ser Lys Leu
                245                 250                 255

Val Leu Lys Ala Leu Cys Thr Lys Val Pro Glu Leu Ile Arg Thr Ile
            260                 265                 270

Met Gly Trp Thr Leu Asp Phe Leu Arg Glu Arg Leu Leu Gly Trp Ile
        275                 280                 285

Gln Asp Gln Gly Gly Trp Asp Gly Leu Leu Ser Tyr Phe Gly Thr Pro
    290                 295                 300

Thr Trp Gln Thr Val Thr Ile Phe Val Ala Gly Val Leu Thr Ala Ser
305                 310                 315                 320

Leu Thr Ile Trp Lys Lys Met Gly
                325

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:Homing
      peptide

<400> SEQUENCE: 7

Cys Leu Ser Ser Arg Leu Asp Ala Cys
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:Homing
      peptide

<400> SEQUENCE: 8

Cys Asn Ser Arg Leu His Leu Arg Cys
 1               5

<210> SEQ ID NO 9
<211> LENGTH: 9
<212> TYPE: PRT
<213> ORGANISM: Artificial Sequence
```

```
<220> FEATURE:
<223> OTHER INFORMATION: Description of Artificial Sequence:Homing
      peptide

<400> SEQUENCE: 9

Cys Glu Asn Trp Trp Gly Asp Val Cys
 1               5

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence:Homing
      peptide

<400> SEQUENCE: 10

Trp Arg Cys Val Leu Arg Glu Gly Pro Ala Gly Gly Cys Ala Trp Phe
 1               5                  10                  15

Asn Arg His Arg Leu
            20

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:Homing
      peptide

<400> SEQUENCE: 11

Cys Leu Pro Val Ala Ser Cys
 1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:Homing
      peptide

<400> SEQUENCE: 12

Cys Gly Ala Arg Glu Met Cys
 1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence:Homing
      peptide

<400> SEQUENCE: 13

Cys Lys Ser Thr His Asp Arg Leu Cys
 1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence:Homing
      peptide

<400> SEQUENCE: 14
```

Cys Gly Asn Lys Arg Thr Arg Gly Cys
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:Homing
      peptide

<400> SEQUENCE: 15

Ala Pro Arg Pro Gly
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence:Homing
      peptide

<400> SEQUENCE: 16

Lys Gln Ala Gly Asp Val
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence:Homing
      peptide

<400> SEQUENCE: 17

Lys Arg Leu Asp Gly Ser
1               5

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence:Homing
      peptide

<400> SEQUENCE: 18

Asp Gly Glu Ala
1

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (1)..(2)
<223> OTHER INFORMATION: n is A, C, G or T

<400> SEQUENCE: 19
nnatcgatcc accatgagca agggcgag                                      28

<210> SEQ ID NO 20
<211> LENGTH: 35
<212> TYPE: DNA

<213> ORGANISM: Artificial Sequence
<220> FEATURE:
<223> OTHER INFORMATION: Description of Artificial Sequence:Primer

<400> SEQUENCE: 20
ctggcaaagt agaaaagggc cttgtacagc tcgtc                    35

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 21
gcccttttct actttgccag                                     20

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (1)..(2)
<223> OTHER INFORMATION: n is A, C, G or T

<400> SEQUENCE: 22
nntctagatc agcccatctt cttcca                              26

<210> SEQ ID NO 23
<211> LENGTH: 57
<212> TYPE: DNA
<213> ORGANISM: Artificial Sequence
<220> FEATURE:
<223> OTHER INFORMATION: Description of Artificial Sequence:Primer

<400> SEQUENCE: 23
ccatggcctg cgattgccgt ggtgattgtt tttgtggtgg tatgagcaag ggcgagg    57

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (1)..(4)
<223> OTHER INFORMATION: n is A, C, G or T

<400> SEQUENCE: 24
nnnnccatgg cctgcgattg cc                                  22

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 25
tggaaaagca ctgcacgc                                       18

<210> SEQ ID NO 26
<211> LENGTH: 45

```
<212> TYPE: DNA
<213> ORGANISM: Artificial Sequence
<220> FEATURE:
<223> OTHER INFORMATION: Description of Artificial Sequence:Primer

<400> SEQUENCE: 26
ccatggcctg caacggtcgt tgcggtggta tgagcaaggg cgagg                45

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (1)..(4)
<223> OTHER INFORMATION: n is A, C, G or T

<400> SEQUENCE: 27
nnnnccatgg cctgcaacgg tc                                         22
```